United States Patent [19]

Battista

[11] Patent Number: 4,676,785
[45] Date of Patent: Jun. 30, 1987

[54] LIQUID RETAINING ABSORBENT STRUCTURE

[76] Inventor: Orlando A. Battista, 3725 Fox Hollow Rd., Fort Worth, Tex. 76109

[21] Appl. No.: 789,425

[22] Filed: Oct. 21, 1985

[51] Int. Cl.$^4$ ............................................. A61F 13/16
[52] U.S. Cl. ................................. 604/369; 604/385.1; 428/72; 428/913
[58] Field of Search ............... 604/358, 366, 370, 374, 604/369, 375, 385.1, 378, 383, 369; 428/68, 72, 73, 116, 178, 913

[56] References Cited

U.S. PATENT DOCUMENTS 3,881,489  5/1975  Hartwell ............................ 604/370
4,173,046  11/1979  Gallagher .......................... 604/375
4,323,069  4/1982  Ahr et al. ........................... 604/375
4,360,021  11/1982  Stima ................................ 604/369

FOREIGN PATENT DOCUMENTS 2406525  8/1974  Fed. Rep. of Germany ...... 604/378

Primary Examiner—John D. Yasko

[57] ABSTRACT

Liquid retaining absorbent structures consisting of a plurality of cells, each cell having an aperture to allow a liquid to enter the cell. The cell contains an expandable absorbent material and a valve member. As liquid enters the cell, the absorbent expands. When the amount of liquid is equivalent to the free volume of the cell the expanding absorbent causes the valve member to seal the aperture to isolate the liquid.

10 Claims, 10 Drawing Figures

LIQUID RETAINING ABSORBENT STRUCTURE

This invention relates to improvements in disposable absorbent products or structures possessing improved liquid retention characteristics.

A wide variety of absorbent products have been proposed for use as sanitary napkins, infant disposable diapers, adult geriatric dressings and diapers, drapes, dressings, bed pads, and the like. In general, these products or structures, include a liquid impermeable base sheet or film, an absorbent batt or pad, and a liquid permeable cover sheet or film. The base sheet or film may consist of a liquid impermeable plastic film such as polyethylene, polypropylene, polyester, polyvinyl chloride, and the like. The absorbent batt or pad may consist of a mass of hydrophilic natural or synthetic fibers such as cotton linters, wood pulp fibers, modified rayons, and the like. The liquid permeable cover sheet or film may consist of a foramenous plastic film, gauze, a non-woven fabric, papaer, and the like.

While these structures may be very absorbent and urine and other body liquids such as exuded by decubitus ulcers and the like are absorbed readily, the absorbed liquid is not isolated. As pressure is applied to the absorbent structure saturated with the liquid, the absorbed liquid is expressed through the permeable cover sheet through which the liquid passed initially into the absorbent batt or pad and thereby comes into contact with the body.

The principle purpose of the present invention is to provide a highly absorbent structure wherein the absorbed liquid is isolated and prevented from being expressed from the structure.

Another purpose of the invention is to provide a highly effective liquid absorbent structure which may be fabricated from readily available inexpensive materials.

A futher purpose of the invention is to provide a highly effective liquid absorbent structure having a liquid impermeable base layer that prevents absorbed liquid to pass to a supporting structure.

Other purposes and advantages of the structures of the present invention will become apparent from the description which follows.

The structures of the present invention comprise a plurality of cells or compartments adapted to receive a liquid and provided with means whereby the cell becomes sealed when the volume of liquid received is equivalent to the free volume of the cell.

In the drawings:

FIGS. 1, 4, and 7 are cross-sectional views of cells formed in accordance with the present invention.

Figure 1:
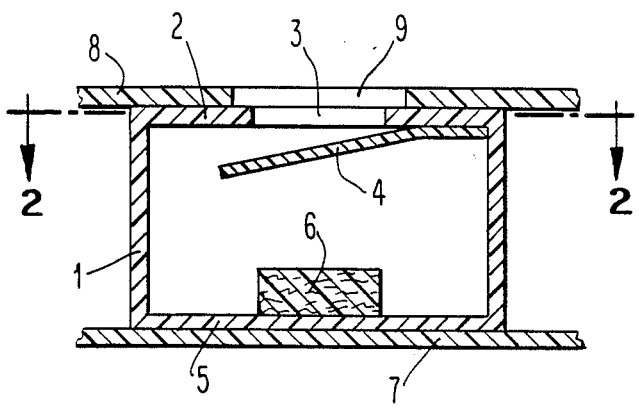
Figure 2:
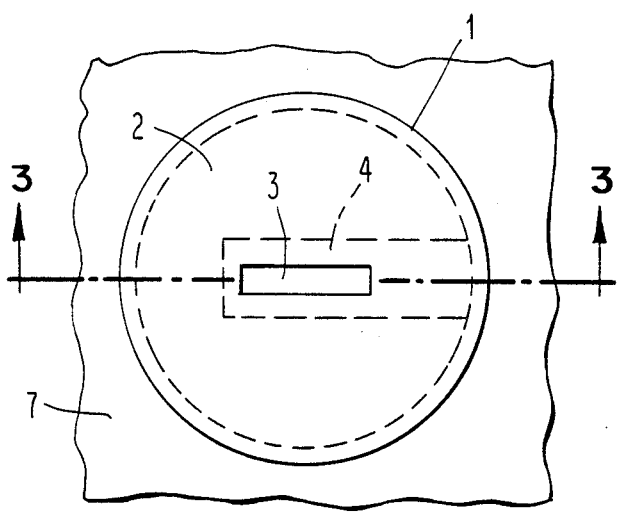
FIG. 2 is a plan view of the cell of FIG. 1 taken on line 2—2.
Figure 3:
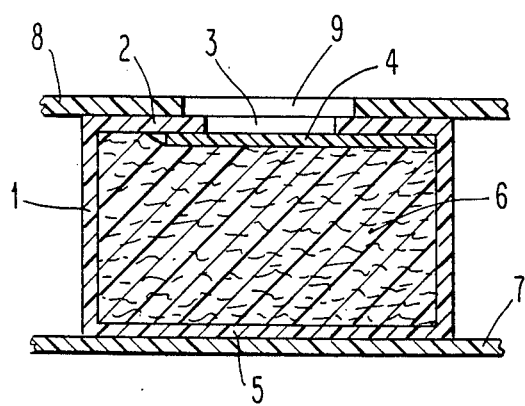
FIG. 3 is a cross-sectional view of the cell of FIGS. 1 and 2 taken on line 3—3 of FIG. 2 after receiving a liquid.

As illustrated in FIGS. 1, 2, and 3, The cell 1 is of closed cylindrical configuration having an upper wall 2 provided with an aperture 3 which may be in the form of a slot. A valve member 4 one end of which is secured to the inner surface of upper wall 2 depends from the upper wall. The area of the depending portion of the valve member 4 is greater than the area of aperture 3 and is adapted to close the aperture. A highly absorbent body 6 is disposed within cell 1 and may be secured to the lower wall 5 of the cell. The body may consist of a compressed absorbent material such as, for example, regenerated cellulose sponge or other polymeric sponge, modified rayon fibers, cellulose derivative fibers such as carboxymethyl cellulose, or any other absorbent and expandable material. As an aqueous liquid passes through aperture 3 and contacts the absorbent body 6, the body absorbs the liquid and expands. When the volume of liquid received by the cell is equivalent to the free volume of the cell, the absorbent body 6 expands to fill the cell and forces the valve 4 into contact with the upper wall 2 thereby sealing the cell as illustrated in FIG. 3, thus preventing the liquid from becoming expressed from the cell. Should pressure be applied to the cell, the body 6 merely increases the pressure on valve member 4 sealing aperture 3. In the event a lesser amount of liquid has passed into the cell, pressure on the cell when formed of flexible material will force valve member 4 into contact with upper wall 2 of the cell and thereby seal aperture 3 to prevent the liquid from being expressed through the aperture.

A plurality of cells 1 are secured to a liquid impermeable base sheet 7 and an upper or covering foramenous sheet 8. The upper sheet is provided with apertures 9 which register with the apertures 3 of the cells. It is obvious that the size and number of cells in the absorbent structure will be based upon the specific use of the structure and the estimated amount of liquid to be absorbed. The cells may be in spaced relationship or may be in contact with adjacent cells. It is also obvious that the amount of absorbent constituting body 6 must be such that when the volume of liquid entering the cell is equivalent to the free volume of the cell the body 6 is capable of expanding sufficiently so as to occupy the entire volume of the cell and thereby force the valve 4 into contact with the upper wall of the cell.

Figure 4:
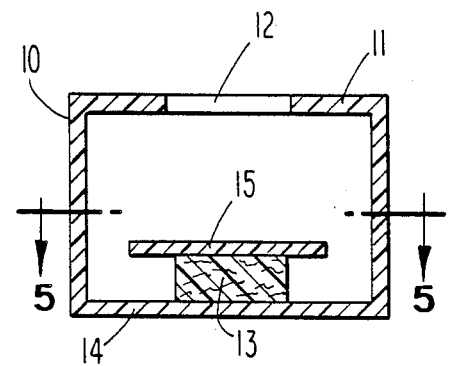
Figure 5:
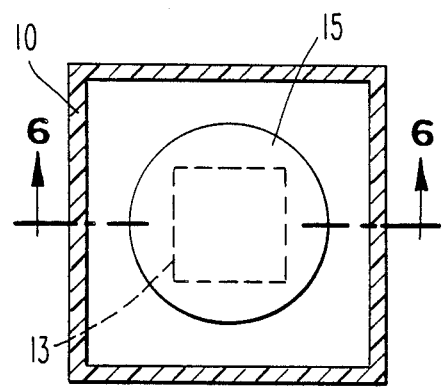
FIG. 5 is a sectional view of the cell of FIG. 4 taken on line 5—5 of FIG. 4.
Figure 6:
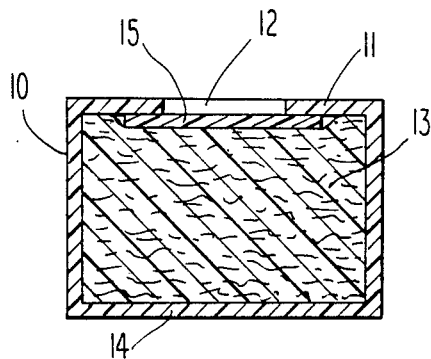
FIG. 6 is a cross-sectional view of the cell of FIGS. 4 and 5 taken on line 6—6 of FIG. 5 after receiving a liquid.

Although the cell of FIGS. 1, 2, and 3 are cylindrical in configuration, the cells may be of any desired configuration. As illustrated in FIGS. 4, 5, and 6, the cell 10 is of cubical configuration. The upper wall 11 is provided with a centrally located circular aperture 12. An absorbent body 13 is secured to the inner surface of the lower wall 14 of the cell. A circular valve member 15 is secured to the upper surface of the absorbent body 13. As shown in FIG. 6, when the body 13 has absorbed liquid and expanded to fill the cell, the valve member 14 seals aperture 12. As described above, the desired number of cells are secured to an impermeable lower sheet and an upper sheet provided with apertures registering with the apertures in the upper walls of the cells.

In producing the cells, the absorbent body may be secured to a blank in the shape and form of the lower cell wall. The upper wall and side walls may be formed as a cup-shaped element and the blank and side walls joined as by means of fusion or an adhesive. Prior to assembling the cells, the valve member 4 is secured to the upper wall 2 of the cells as illustrated in FIG. 1, or the valve member 15 secured to the absorbent body 13 as shown in FIG. 4.

Figure 7:
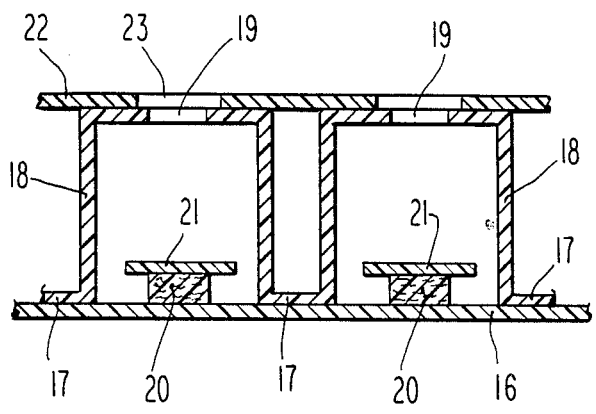
FIG. 7 is a cross-sectional view illustrating a futher form of cell in accordance with the invention.

Although independent cells have been described, the cells may be formed from a pair of plastic sheets as illustrated in FIG. 7. The base consists of an impermeable sheet 16. A second sheet 17 is molded or cast to form a plurality of cells 18, the upper wall of the cell having an aperture 19. Compressed absorbent elements 20 carrying valve members 21 are secured to the base sheet 16 in a spaced relationship corresponding to the spacing of the cells. The sheet 17 with the preformed cells 18 is secured to the base sheet 16 as by fusion or with an adhesive. A cover sheet 22 having apertures 23 which register with the apertures 19 in the cells 18 is secured to the top walls of the cells as by fusion or with an adhesive.

Figure 8:
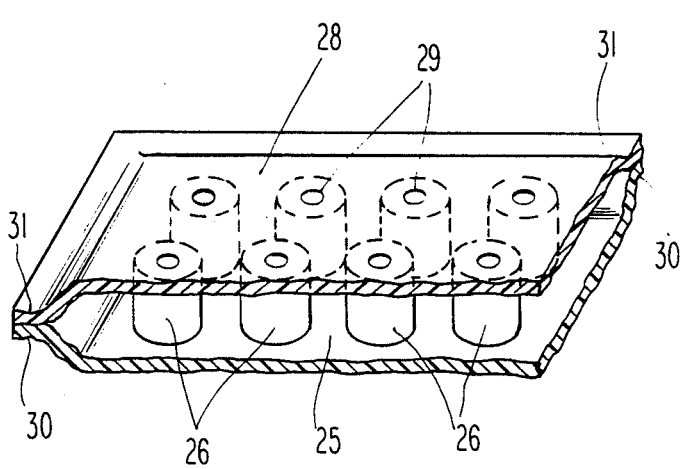
FIG. 8 is an isometric view of a portion of an absorbent structure formed in accordance with the invention.

As shown in FIG. 8, the absorbent structure comprises a base sheet 25, a plurality of spaced cells 26, each cell having an aperture in its upper wall, and an upper sheet 28 having spaced apertures 29 which register with the cell apertures. As described above, a compressed absorbent element and associated valve member is disposed in each of the cells or compartments. The marginal portions 30 at the ends and along the sides of the base sheet 25 and the marginal portions 31 at the ends and along the sides of the upper sheet 28 are brought together and sealed as by fusion or with an adhesive. Thus the ends and sides of the base and the cover sheet are fixed relative to each other to form an envelope.

Figure 9:
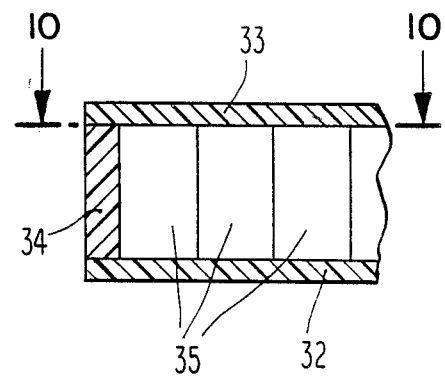
FIG. 9 is a sectional view of a futher form of absorbent structure taken on line 9—9 of FIG. 10.
Figure 10:
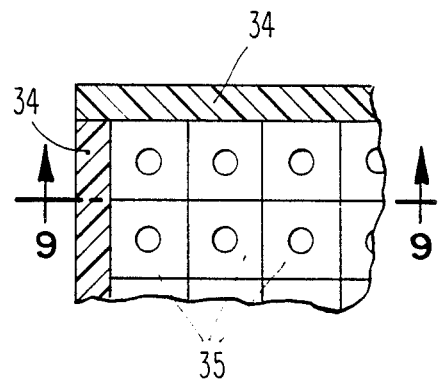
FIG. 10 is a sectional view taken on line 10—10 of FIG. 9.

In the structure shown in FIGS. 9 and 10, the base impermeable sheet 32 and upper foramenous sheet 33 are maintained in a desired spaced relationship at their ends and along their sides by suitable spacing members 34 secured to the sheets along the marginal areas of the sheets. These members may be formed of suitable flexible and pliable hydrophobic materials such as polyurethane foam or sponge and, in effect, form a framed area. A plurality of cells 35, such as, for example, those illustrated in FIG. 4, are disposed in contiguous arrangement within the framed area. Similar to the structure shown in FIG. 8, the ends and the sides of the base sheet and upper or cover sheet are maintained in fixed relationship to form an envelope within which the cells are disposed.

It is obvious that the size of the structure and the size of the cells or compartments will be dictated by the specific use of the structure. A structure desired for a small wound where the liquid exudate will be small will comprise relatively small cells. A structure desired as a bed pad will comprise relatively large cells for the absorption of large amounts of liquid exudate. The preferred absorbent material is highly compressed regenerated cellulose sponge because of its high absorbency, ready availability, low cost, and high expansion when met with aqueous liquids.

In order to simplify the description, the terms "upper" and "lower" and "base sheet" and "cover sheet" have been used to indicate relationships and not as limitations. The terms "upper" and "cover sheet" have been used to designate the face of the structure through which the liquid passes to the cells.

What is claimed is:

1. A liquid retaining absorbent structure comprising a plurality of cells each of the cells having an aperture in its upper wall through which a liquid may pass into the cell, a valve member within each cell and an expandable, absorbent, hydrophilic material within each cell adapted to expand and to move the valve member to close the aperture when the volume of liquid passing into the cell is equivalent to the free volume of the cell.

2. The structure as defined in claim 1 wherein the valve member is secured to the upper surface of the expandable, absorbent, hydrophilic material.

3. The structure as defined in claim 1 wherein the expandable, absorbent, hydrophilic material is compressed regenerated cellulose sponge.

4. The structure as defined in claim 1 wherein the cells are secured to a liquid impermeable base sheet and to a foramenous cover sheet, the cover sheet having apertures registering with the apertures of the cells.

5. The structure as defined in claim 4 wherein the ends and the sides of the base and cover sheets are fixed relative to each other to form an envelope.

6. The structure as defined in claim 2 where in the expandable, absorbent material is regenerated cellulose sponge.

7. The structure as defined in claim 2 wherein the cells are secured to a liquid impermeable base sheet and to a foramenous cover sheet, the cover sheet having apertures registering with the apertures of the cells.

8. The structure as defined in claim 7 wherein the ends and the sides of the base and cover sheets are fixed relative to each other to form an envelope.

9. The structure as defined in claim 3 wherein the cells are secured to a liquid impermeable base sheet and to a foramenous cover sheet, the cover sheet having apertures registering with the apertures of the cells.

10. The structure as defined in claim 9 wherein the ends and the sides of the base and cover sheets are fixed relative to each other to form an envelope.

* * * * *